(12) United States Patent
Bae et al.

(10) Patent No.: US 10,695,090 B2
(45) Date of Patent: Jun. 30, 2020

(54) AUTOMATIC HAIR TRANSPLANT APPARATUS

(71) Applicants: ELECTRONICS AND TELECOMMUNICATIONS RESEARCH INSTITUTE, Daejeon (KR); KYUNGPOOK NATIONAL UNIVERSITY INDUSTRY-ACADEMIC COOPERATION FOUNDATION, Daegu (KR)

(72) Inventors: Tae Wuk Bae, Daegu (KR); Yong Chul Jung, Daegu (KR); Moon Kyu Kim, Daegu (KR); Jung Chul Kim, Daegu (KR); Kyu Hyung Kim, Daegu (KR); Jung Wook Suh, Daegu (KR); Soo In Lee, Daegu (KR); Hyung Soo Lee, Daejeon (KR); Eun Chang Choi, Daegu (KR)

(73) Assignees: ELECTRONICS AND TELECOMMUNICATIONS RESEARCH INSTITUTE, Daejeon (KR); KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 264 days.

(21) Appl. No.: 15/867,352

(22) Filed: Jan. 10, 2018

(65) Prior Publication Data

US 2018/0193058 A1   Jul. 12, 2018

(30) Foreign Application Priority Data

Jan. 10, 2017   (KR) .................. 10-2017-0003468
Dec. 14, 2017   (KR) .................. 10-2017-0172441

(51) Int. Cl.
*A61B 17/34*        (2006.01)
*A61F 2/10*         (2006.01)

(52) U.S. Cl.
CPC ...... *A61B 17/3468* (2013.01); *A61B 17/3421* (2013.01)

(58) Field of Classification Search
CPC . A61B 17/34; A61B 17/3468; A61B 17/3421; A61B 17/32053; A61F 2/10; A61F 2017/00969; A61F 2017/00752
See application file for complete search history.

(56) References Cited

U.S. PATENT DOCUMENTS 5,439,475 A *  8/1995  Bennett .............. A61B 17/3468
                                                606/187
8,753,354 B2 * 6/2014  Cole ................ A61B 17/32053
                                                606/131

(Continued)

FOREIGN PATENT DOCUMENTS

KR       20-0470718 Y1    1/2014
KR    10-2018-0142691 A  12/2016

*Primary Examiner* — Vi X Nguyen

(57) ABSTRACT

Disclosed is an automatic hair transplant apparatus including a needle module in which a hair follicle is inserted, a supplying case which has a magazine shape into which the needle module is inserted like a bullet of a gun, a withdrawing case which has a magazine shape into which the needle module is inserted like a bullet of a gun, and a hair transplanter on which the supplying case and the withdrawing case are mounted and which transplants hair follicles into a scalp by sequentially operating needle modules in the supplying case one by one and inserts needle modules from which hair follicles are removed into the withdrawing case.

11 Claims, 9 Drawing Sheets

(56) References Cited

U.S. PATENT DOCUMENTS

2016/0015424 A1 1/2016 Kim et al.
2016/0045223 A1 2/2016 Kim et al.

* cited by examiner

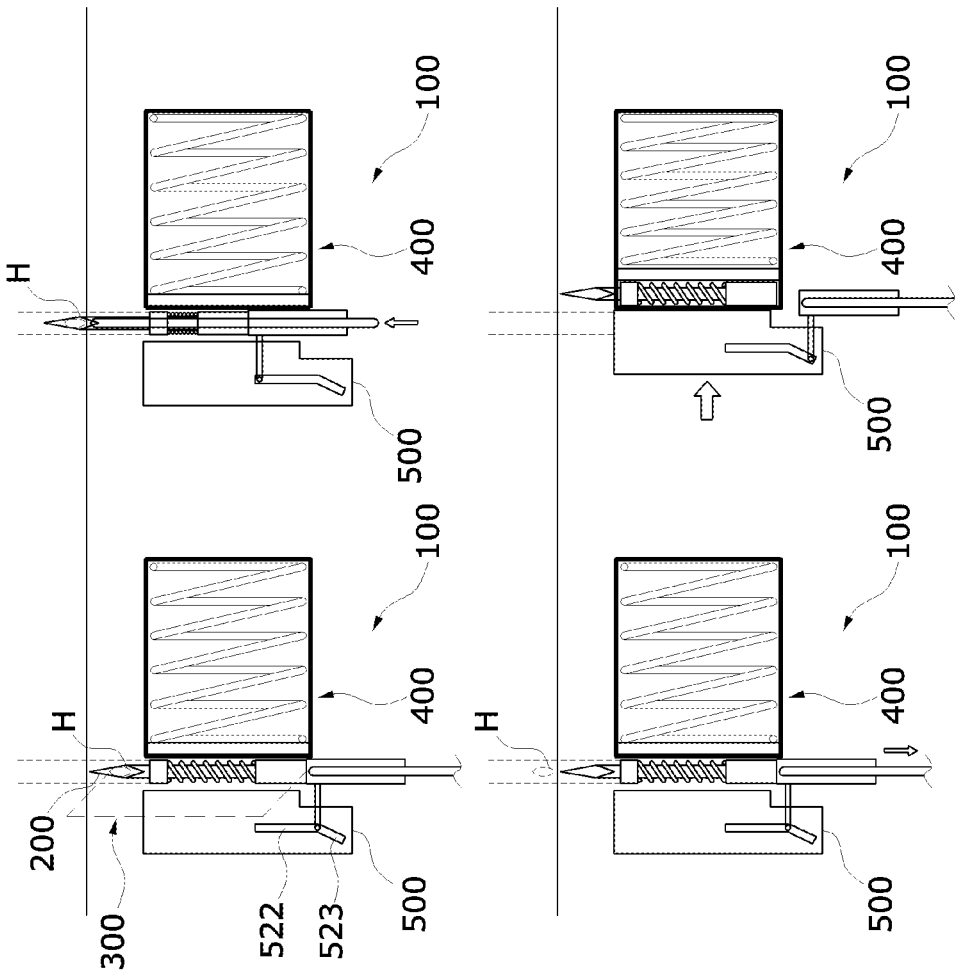

AUTOMATIC HAIR TRANSPLANT APPARATUS

CROSS-REFERENCE TO RELATED APPLICATION

This application claims priority to and the benefit of Korean Patent Application No. 10-2017-0003468, filed on Jan. 10, 2017, and 10-2017-0172441, filed on Dec. 14, 2017, the disclosure of which is incorporated herein by reference in its entirety.

BACKGROUND

1. Field of the Invention

The present invention relates to an automatic hair transplant apparatus, and more particularly, to an automatic hair transplant apparatus configured to perform continuous transplantation to replace an existing manual hair transplant apparatus.

2. Discussion of Related Art

In current hair transplantation, a nurse mounts only one hair follicle in each hair transplant needle and a surgeon, who is the transplantation operator, performs a hair transplant using a manual hair transplant apparatus in which the hair follicle is mounted.

In the case of a currently used manual hair transplant apparatus, since about 2,000 grafts are performed on one patient in one operation, fatigue of both the patient and the surgeon increases and 3 to 4 hours are consumed for the operation.

As described above, transplantation of hair follicles using a manual hair transplant apparatus has much inconvenience in operation time or costs charged to the patient. Although, apparatuses capable of automatically/semiautomatically transplanting a hair follicle have been studied to overcome the limitation, commercialization of such apparatuses has failed.

SUMMARY OF THE INVENTION

Therefore, it is an aspect of the present invention to provide an automatic hair transplant apparatus capable of easily and continuously transplanting hair follicles by configuring a needle module in which the hair follicles are inserted and a case in which the needle module is mounted to be a magazine structure.

According to one aspect of the present invention, an automatic hair transplant apparatus includes a needle module in which a hair follicle is inserted, a supplying case which has a magazine shape into which the needle module is inserted like a bullet of a gun, a withdrawing case which has a magazine shape into which the needle module is inserted like a bullet of a gun, and a hair transplanter on which the supplying case and the withdrawing case are mounted and which transplants hair follicles into a scalp by sequentially operating needle modules in the supplying case one by one and inserts needle modules from which hair follicles are removed into the withdrawing case.

BRIEF DESCRIPTION OF THE DRAWINGS

The above and other objects, features, and advantages of the present invention will become more apparent to those of ordinary skill in the art by describing exemplary embodiments thereof in detail with reference to the accompanying drawings, in which:

FIGS. 6 and 7 are views illustrating states in which the automatic hair transplant apparatus according to one embodiment of the present invention is used.

DETAILED DESCRIPTION OF EXEMPLARY EMBODIMENTS

Advantages and features of the present disclosure and a method of achieving the same will become apparent with reference to the attached drawings and the embodiments described below in detail. However, the present invention is not limited to the embodiments described below, and may be embodied with a variety of different modifications. The embodiments are merely provided to allow one of ordinary skill in the art to completely understand the scope of the present invention, and are defined by the claims. Meanwhile, the terms used herein are for explaining embodiments and are not intended to limit the present invention. Throughout the specification, unless particularly defined otherwise, singular forms include plural forms. The terms "comprises" and/or "comprising" are used herein with meanings which include the stated components, stages, operations, and/or elements while not excluding the presence or addition of one or more other components, stages, operations, and/or elements.

Figure 1:
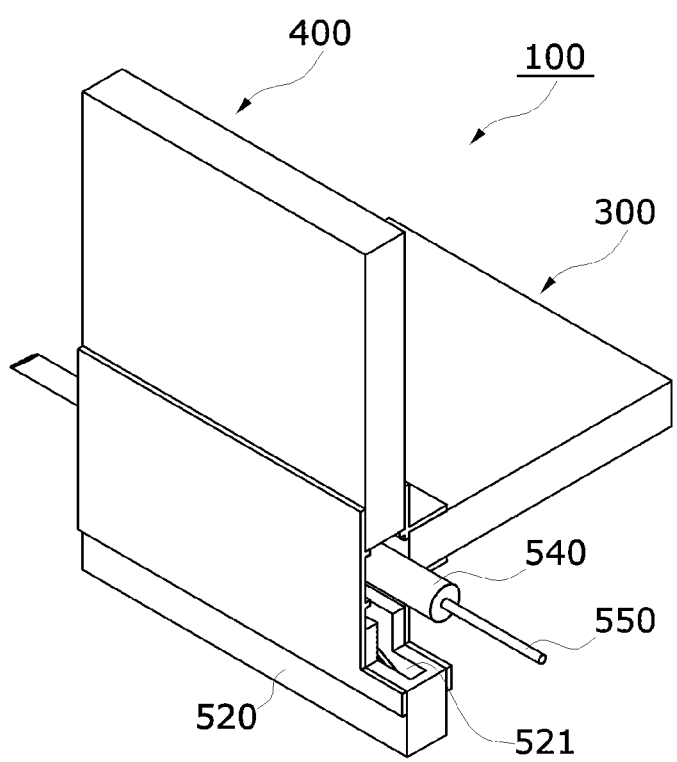
FIG. 1 is a perspective view of an automatic hair transplant apparatus according to one embodiment of the present invention.
Figure 2:
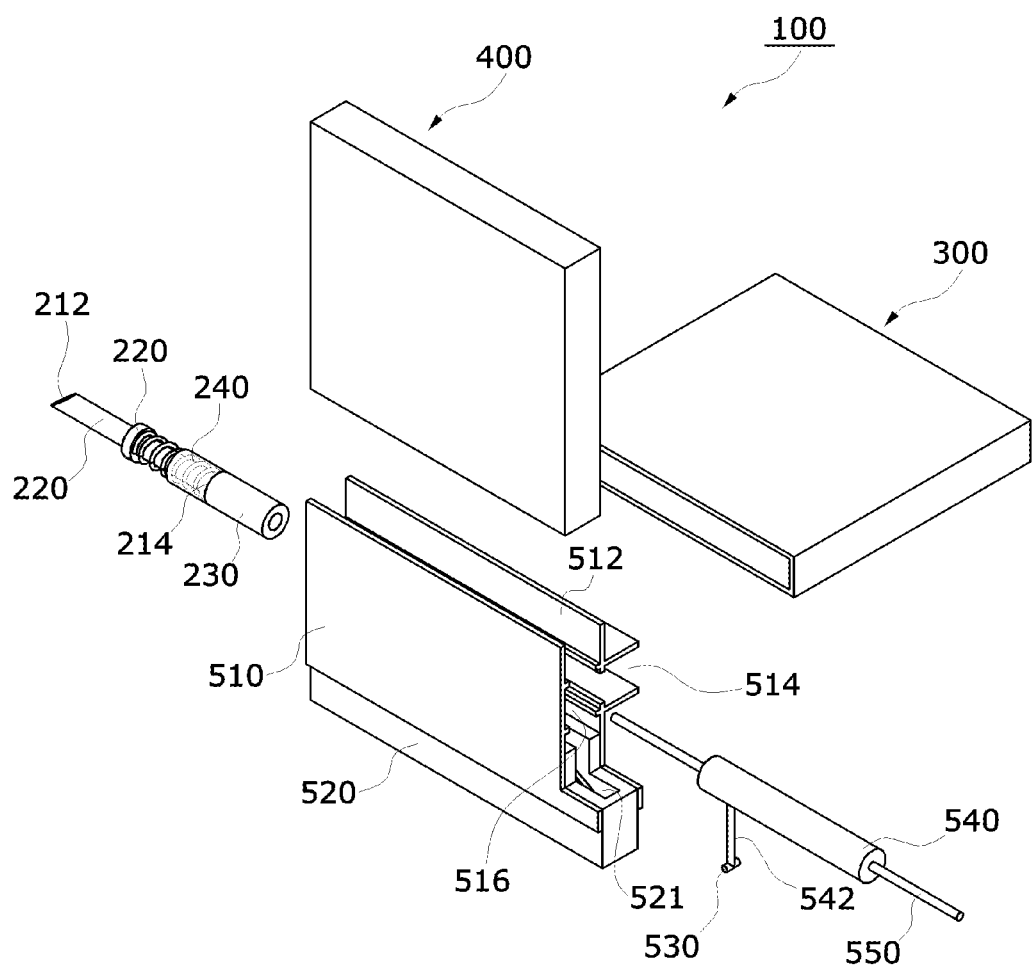
FIG. 2 is a disassembled perspective view of the automatic hair transplant apparatus according to one embodiment of the present invention.
Figure 3A:
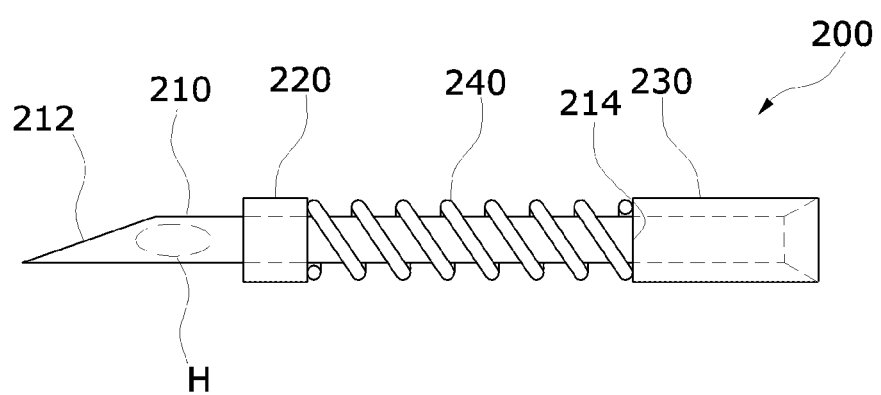
FIGS. 3A and 3B are views illustrating operation states of a needle module which forms the automatic hair transplant apparatus according to one embodiment of the present invention.
Figure 3B:
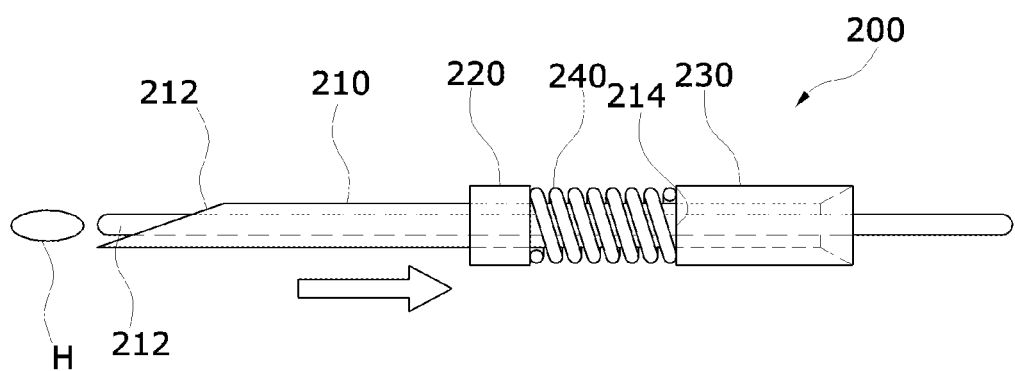
Figure 4:
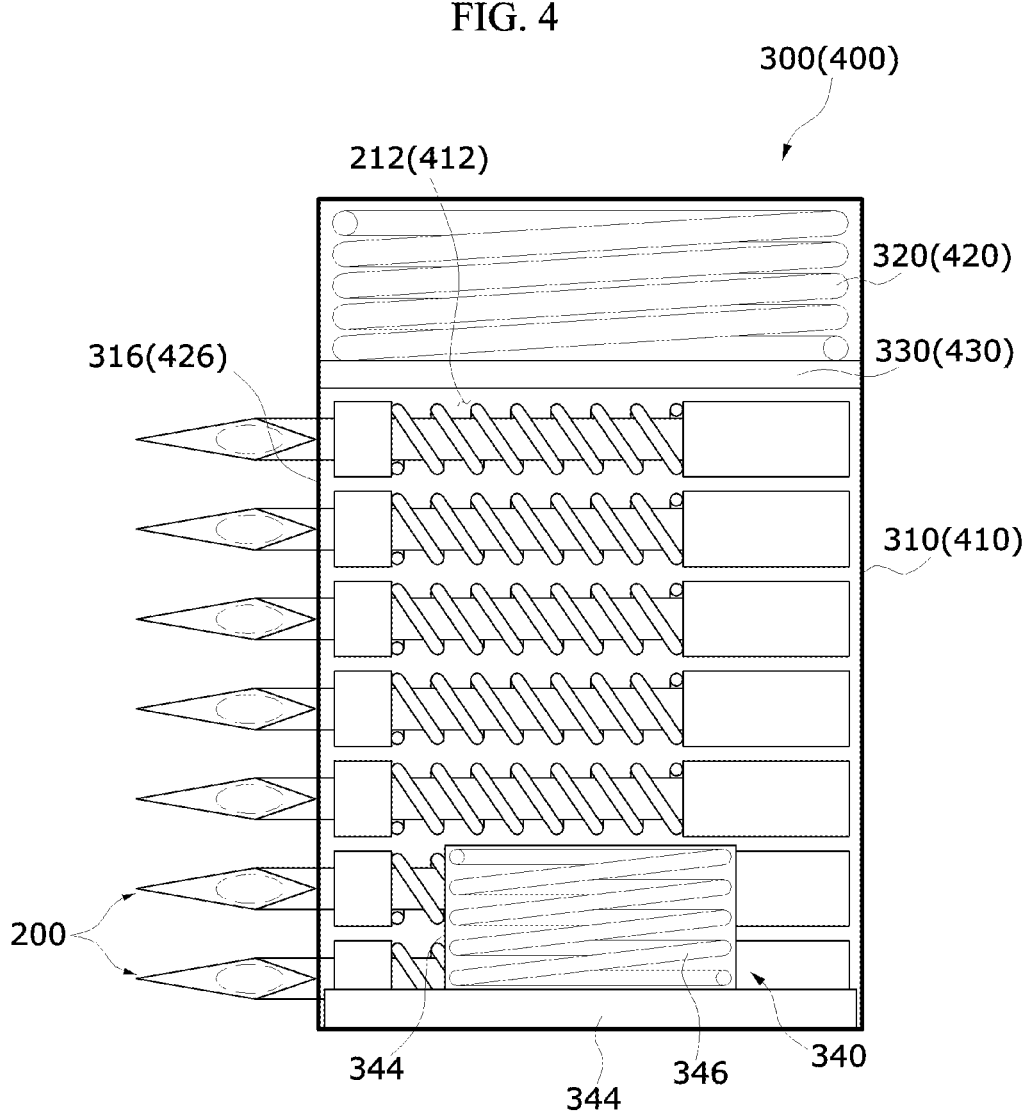
FIG. 4 is a front view illustrating a supplying case and a withdrawing case of the automatic hair transplant apparatus according to one embodiment of the present invention.
Figure 5A:
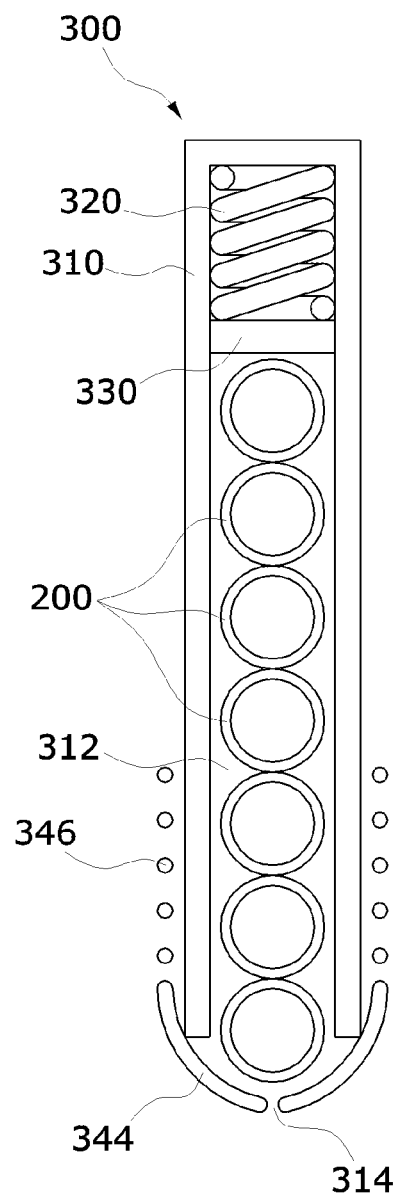
FIGS. 5A and 5B are side views illustrating a case which forms the automatic hair transplant apparatus according to one embodiment of the present invention.
Figure 5B:
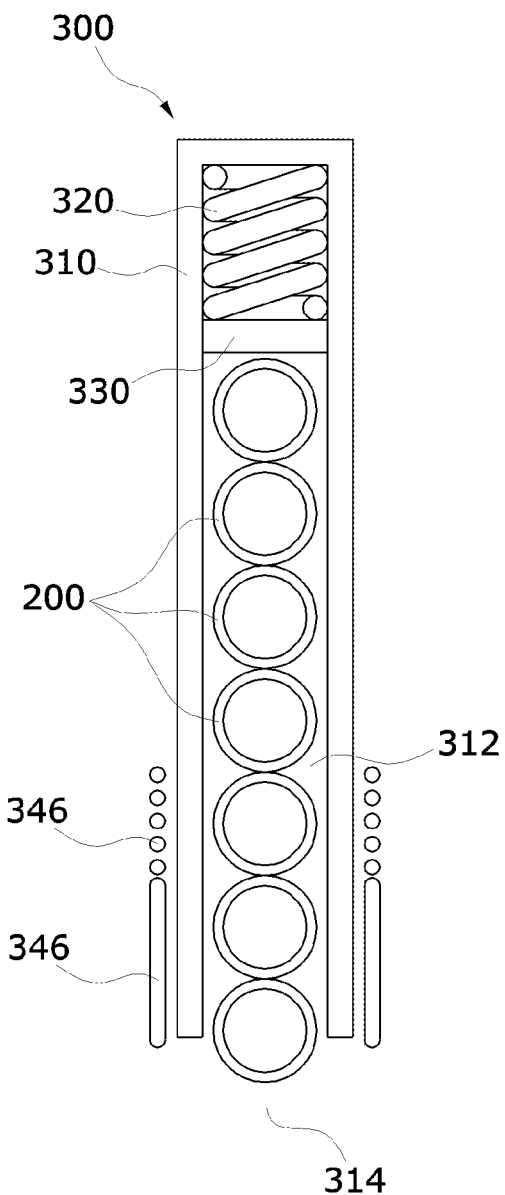
Figure 7:
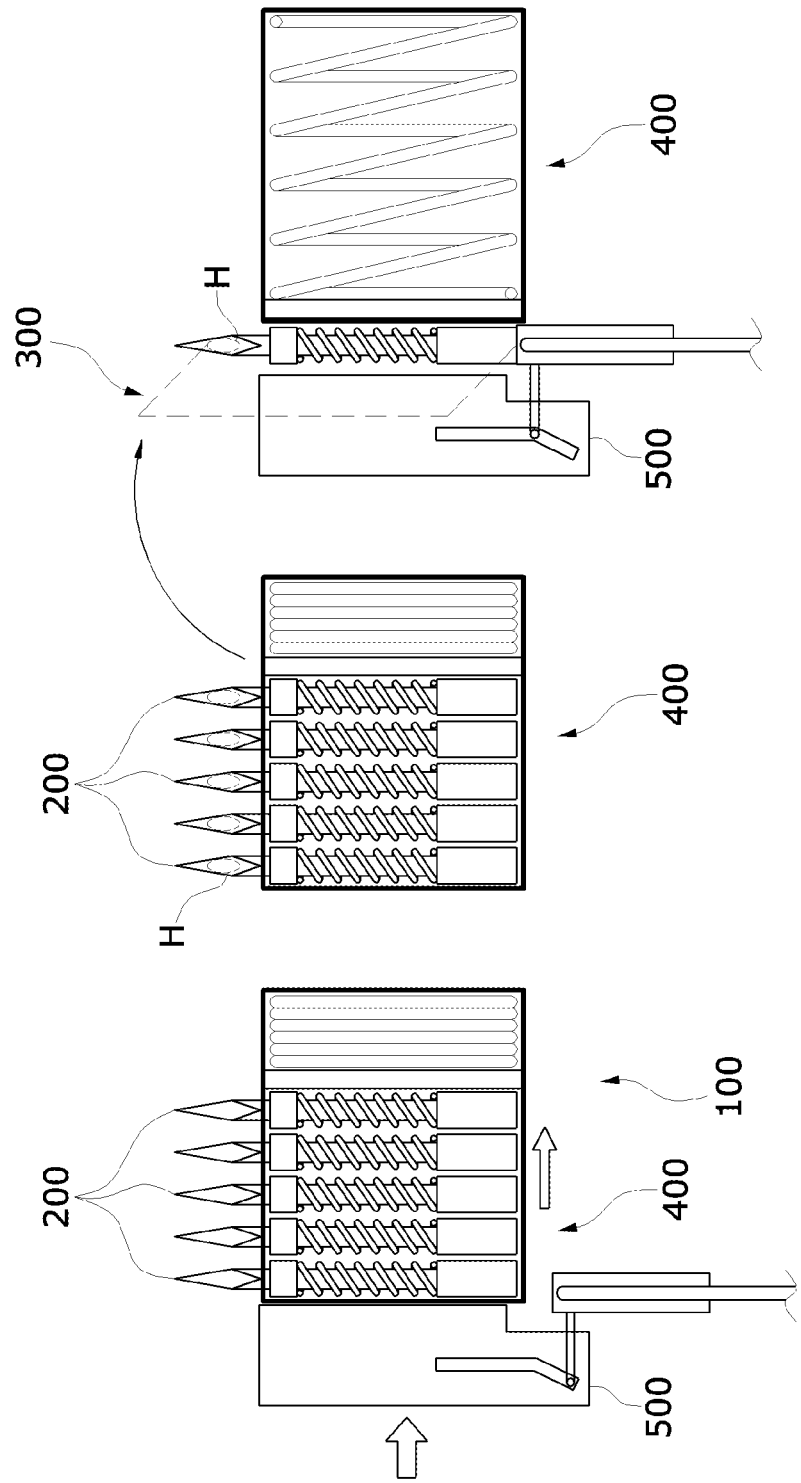

Hereinafter, exemplary embodiments of the present invention will be described in detail with reference to the attached drawings. FIG. 1 is a perspective view of an automatic hair transplant apparatus according to one embodiment of the present invention. FIG. 2 is a separate-perspective view of the automatic hair transplant apparatus according to one embodiment of the present invention. FIGS. 3A and 3B are views illustrating operation states of a needle module which forms the automatic hair transplant apparatus according to one embodiment of the present invention. FIG. 4 is a front view illustrating a supplying case and a withdrawing case of the automatic hair transplant apparatus according to one embodiment of the present invention. FIGS. 5A and 5B are side views illustrating a case which forms the automatic hair transplant apparatus according to one embodiment of the present invention.

An automatic hair transplant apparatus 100 according to one embodiment of the present invention includes a needle module 200, a supplying case 300, a withdrawing case 400, and a hair transplanter 500.

A hair follicle H is inserted into the needle module 200.

Also, the needle module 200 includes a needle 210 formed in a hollow shape with an inclined or pointed front end 212, a front end fixing device 220 having a hollow shape and inserted into the front end 212 of the needle 210, a rear end fixing device 230 having a hollow shape and fixedly coupled to the other end 214 of the needle 210, and a spring 240 mounted on an outer surface of the needle 210 and located between the front end fixing device 220 and the rear end fixing device 230.

Here, the front end fixing device 220 and the rear end fixing device 230 have the same diameters to smoothly move and operate, and a front end of the spring 240 is fixed to the front end fixing device 220.

That is, the needle module 200 in which the front end fixing device 220, to which one end of the spring 240 is fixed, is mounted on a front end part of the needle 210 formed in a hollow shape and the rear end fixing device 230 mounted on a rear end of the needle 210, and is moved forward depending on whether the rear end fixing device 230 is pressurized.

In more detail, the needle module 200 maintains its initial state due to an elasticity of the spring 240, and the spring 240 is compressed and the needle 210 is moved toward a scalp when the rear end fixing device 230 is pressurized.

The supplying case 300 is mounted on one side of the hair transplanter 500, and a plurality of such needle modules 200 are mounted therein.

That is, the supplying case 300 is mounted on the one side of the hair transplanter 500 and sequentially supplies the needle modules 200 mounted therein thereto.

Also, the supplying case 300 includes a cover 310 in which an accommodation space 312 is formed and an opening 314 is formed at a bottom or top thereof, a pressurizing spring 320 inserted into the accommodation space 312 and located opposite the opening 314 of the cover 310, and a support plate 330 mounted in the accommodation space 312 and located between the pressurizing spring 320 and the opening 314.

Here, a module guide groove 316 is formed at a front end of the cover 310 in a longitudinal direction to prevent damage to the needle 210 of the needle module 200.

That is, in the supplying case 300, the pressurizing spring 320 and the support plate 330 are sequentially mounted in the cover 310 which includes the accommodation space 312 formed therein, the opening 314 formed at the bottom or top thereof, and the module guide groove 316 formed at the front end in the longitudinal direction.

In more detail, the supplying case 300 is formed in a magazine shape into which the needle module 200 is inserted like a bullet of a gun.

Next, an opening and closing portion 340 which closes and opens the accommodation space 312 may be further included in the opening 314 of the cover 310.

Here, the opening and closing portion 340 includes an opening and closing case 342 mounted at a central part of both sides of the cover 310 and having an open bottom, a curved guide 344 having a curved shape and disposed on each of both sides of the opening 314 and located partially in the opening and closing case 342, and an opening and closing spring 346 disposed at an end of the curved guide 344 and in the opening and closing case 342.

That is, in the opening and closing portion 340, the curved guide 344 usually blocks the opening 314 due to an elasticity of the opening and closing spring 346, and the curved guide 344 is inserted into the opening and closing case 342 and the opening 314 is opened when an external force greater than the elasticity of the opening and closing spring 346 is transferred to an end of the curved guide 344 on an opposite side.

The withdrawing case 400 is mounted on the other side of the hair transplanter 500, and a plurality of such needle modules 200 from which hair follicles H are removed are mounted therein.

That is, the withdrawing case 400 is mounted on the other side of the hair transplanter 500 and sequentially accommodates the needle modules 200 from which the hair follicles H are removed according to an operation of the hair transplanter 500.

Also, the withdrawing case 400 includes a cover 410 in which an accommodation space 412 is formed and an opening 414 is formed at a bottom or top thereof, a pressurizing spring 420 inserted into the accommodation space 412 and located opposite the opening 414 of the cover 410, and a support plate 430 mounted in the accommodation space 412 and located between the pressurizing spring 420 and the opening 414.

Here, a module guide groove 416 is formed at a front end of the cover 410 in a longitudinal direction to prevent damage to the needle 210 of the needle module 200.

That is, in the withdrawing case 400, the pressurizing spring 420 and the support plate 430 are sequentially mounted in the cover 410 which includes the accommodation space 412 formed therein, the opening 414 formed at the bottom or top thereof, and the module guide groove 416 formed at the front end in the longitudinal direction.

In more detail, the withdrawing case 400, like the supplying case 300, is formed in a magazine shape in which the needle module 200 is inserted like a bullet of a gun.

The supplying case 300 and the withdrawing case 400 are mounted on the hair transplanter 500.

That is, the hair transplanter 500 sequentially operates the needle modules 200 inserted into the supplying case 300 one by one to transplant the hair follicles H into the scalp, and inserts the needle modules 200, from which the hair follicles H are removed, into the withdrawing case 400.

Also, the hair transplanter 500 includes a hair transplanter case 510 in which a withdrawing case mounting groove 512 and a body mounting groove 514 are collinearly formed and a supplying case mounting groove 516 is rectilinearly or obliquely formed between the withdrawing case mounting groove 512 and the body mounting groove 514, a body 520 which is mounted on the body mounting groove 514, linearly moves, and includes a roller guide groove 521 formed at a rear thereof, a moving device 530 formed of any one or a combination of a roller, a ball, an opening, and a bearing mounted on the roller guide groove 521 of the body 520, a main shaft 540 which has a hollow shape and an outer surface to which a connecting rod 542, which has one end coupled to the moving device 530, is fixedly coupled, and a pressurizing bar 550 which is inserted into the main shaft 540 and pressurizes and transplants the hair follicle H into the scalp.

That is, in the case of the hair transplanter 500, the withdrawing case 400 is mounted on the withdrawing case mounting groove 512 of the hair transplanter case 510, the body is mounted on the body mounting groove 514, and the supplying case 300 is mounted on the supplying case mounting groove 516. The needle module 200 with the hair follicle H mounted therein and supplied to the supplying case 300 is moved using the moving device 530 and the main shaft 540. The hair follicle H is transplanted into the scalp using the pressurizing bar 550. The moving device 530, the main shaft 540, and the pressurizing bar 550 are allowed to return to their original states. The needle module 200 from which the hair follicle H is removed is transferred to the withdrawing case 400 by the body 520 being operated.

The new needle module 200 in which the hair follicle H is mounted is prepared using the supplying case 300.

Here, the roller guide groove 521 formed at the body 520 includes a linear portion 522 formed therein and an inclined portion 523 formed at a rear end for a smooth movement and a peripheral disposition of the main shaft 540 according to the operation of the moving device 530.

That is, the moving device 530 and the main shaft 540 move along the inclined portion 523 and the linear portion 522 while the hair follicle H is inserted into the scalp, and move along the linear portion 522 and the inclined portion 523 while the needle module 200 is withdrawn therefrom.

An example of the automatic hair transplant apparatus configured as described above will be described below.

Also, a plurality of such needle modules 200, which each include the needle 210 formed in a hollow shape with the inclined or pointed front end 212, the front end fixing device 220 having a hollow shape and inserted into the front end 212 of the needle 210, the rear end fixing device 230 having a hollow shape and fixedly coupled to the other end 214 of the needle 210, and the spring 240 mounted on the outer surface of the needle 210 and located between the front end fixing device 220 and the rear end fixing device 230, are formed.

Also, the supplying case 300, which includes the cover 310 in which the accommodation space 312 is formed and the opening 314 is formed at the bottom or top thereof, the pressurizing spring 320 inserted into the accommodation space 312 and located opposite the opening 314 of the cover 310, and the support plate 330 mounted in the accommodation space 312 and located between the pressurizing spring 320 and the opening 314, is formed.

Also, the withdrawing case 400, which includes the cover 410 in which the accommodation space 412 is formed and the opening 414 is formed at the bottom or top thereof, the pressurizing spring 420 inserted into the accommodation space 412 and located opposite the opening 414 of the cover 410, and the support plate 430 mounted in the accommodation space 412 and located between the pressurizing spring 420 and the opening 414, is formed.

Also, the hair transplanter 500, which includes the hair transplanter case 510 in which the withdrawing case mounting groove 512 and the body mounting groove 514 are collinearly formed and the supplying case mounting groove 516 is rectilinearly or obliquely formed between the withdrawing case mounting groove 512 and the body mounting groove 514, the body 520 which is mounted on the body mounting groove 514, linearly moves, and includes the roller guide groove 521 formed at the rear thereof, the moving device 530 formed of any one or a combination of a roller, a ball, an opening, and a bearing mounted on the roller guide groove 521 of the body 520, the main shaft 540 which has the hollow shape and the outer surface to which the connecting rod 542 with one end coupled to the moving device 530 is fixedly coupled, and the pressurizing bar 550 which is inserted into the main shaft 540 and pressurizes and transplants the hair follicle H into the scalp, is formed.

Next, the plurality of needle modules 200 in which the hair follicles H are mounted are mounted in the accommodation space 312 of the supplying case 300, and then the supplying case 300 in which the plurality of needle modules 200 are provided is mounted on the supplying case mounting groove 516 of the hair transplanter.

Also, when the body 520 with the moving device 530, the main shaft 540, and the pressurizing bar 550 provided thereon is mounted on the body mounting groove of the hair transplanter 500 and the withdrawing case 400 is mounted on the withdrawing case mounting groove 512, the automatic hair transplant apparatus 100 is completely assembled.

Here, the assembly order of the automatic hair transplant apparatus may differ from the above description. Also, other components in addition to the above-described components may be configured by selecting well-known components of a hair transplant apparatus, and additional descriptions thereof will be omitted.

Next, a case in which the hair follicle H is transplanted into a scalp using the automatic hair transplant apparatus 100 will be described as follows.

First, the opening 314 is opened by the opening and closing portion 340 of the supplying case 300 being operated, and the needle module 200 in which the hair follicle H is mounted and which is mounted therein is moved to an operation position.

Next, the needle module 200 in which the hair follicle H is mounted is moved forward and pushed toward the scalp according to operations of the body 520, the moving device 530, and the main shaft 540 of the hair transplanter 500.

Here, the moving device 530, the main shaft 540, and the pressurizing bar 550 remain in a state of being moved toward the front end.

Also, when the front end 212 of the needle module 200 pricks the scalp, a forward movement of the pressurizing bar 550 stops and the moving device 530, the main shaft 540, and the needle module 200 are moved backward such that the hair follicle H is stably mounted in the scalp.

Next, when the pressurizing bar 550 is removed and returns to its initial state, the body 520 is linearly moved to transfer the needle module 200 from which the hair follicle H is removed to the accommodation space 412 of the withdrawing case 400.

Here, the moving device 530 and the main shaft 540 are moved to the inclined portion 523 of the roller guide groove 521.

Also, when the needle module 200 is completely withdrawn into the withdrawing case 400, the withdrawing case 400 is separated and then the hair follicles H are mounted in the needle modules 200 of the withdrawing case 400.

Afterwards, a circulation process in which the withdrawing case 400 becomes the supplying case 300 and is mounted as the supplying case 300 in the supplying case mounting groove 516 of the hair transplanter 500 is performed.

According to the embodiments of the present invention, an automatic hair transplant apparatus includes a needle module in which a hair follicle is inserted and a case in which the needle module is mounted, which are configured to be a magazine structure, and thus not only may hair follicles be easily and continuously transplanted but also an operation time may be reduced according thereto.

Although the technical concept of the present invention has been exemplarily described above, a variety of modifications may be made thereto by one of ordinary skill in the art without departing from the essential features of the present invention.

Accordingly, the above-described embodiments of the present invention are not intended to limit but to explain the technical concept of the present invention, and the scope of the present invention is not limited thereto. It should be understood that the scope of the present invention is defined by the following claims, and equivalents thereof are included in the scope of the present invention.

What is claimed is:

1. An automatic hair transplant apparatus comprising:
a needle module in which a hair follicle is inserted;

a supplying case which has a magazine shape into which the needle module is inserted like a bullet of a gun;
a withdrawing case which has a magazine shape into which the needle module is inserted like a bullet of a gun; and
a hair transplanter on which the supplying case and the withdrawing case are mounted and which transplants hair follicles into a scalp by sequentially operating needle modules in the supplying case one by one and inserts needle modules from which hair follicles are removed into the withdrawing case,
wherein each of the supplying case and the withdrawing case comprises:
a cover which comprises an accommodation space formed therein and an opening formed at a top or bottom thereof;
a pressurizing spring inserted into the accommodation space and located opposite the opening of the cover; and
a support plate mounted in the accommodation space and located between the pressurizing spring and the opening.

2. The apparatus of claim 1, wherein the needle module comprises:
a needle which has a hollow shape with an inclined or pointed front end;
a front end fixing device which has a hollow shape and is inserted into a front end part of the needle;
a rear end fixing device which has a hollow shape and is fixedly coupled to the other end of the needle; and
a spring mounted on an outer surface of the needle and located between the front end fixing device and the rear end fixing device.

3. The apparatus of claim 2, wherein the front end fixing device and the rear end fixing device have the same diameter.

4. The apparatus of claim 2, wherein a front end of the spring is fixed to the front end fixing device.

5. The apparatus of claim 1, wherein a module guide groove is formed at a front end of the cover in a longitudinal direction.

6. The apparatus of claim 1, further comprising an opening and closing portion formed at the opening of the cover to close and open the accommodation space.

7. The apparatus of claim 6, wherein the opening and closing portion comprises:
an opening and closing case which is mounted on a central part of both sides of the cover and has an open bottom;
a curved guide which has a curved shape, is disposed on each of both sides of the opening, and is located partially in the opening and closing case; and
an opening and closing spring disposed at an end of the curved guide and in the opening and closing case.

8. An automatic hair transplant apparatus comprising:
a needle module in which a hair follicle is inserted;
a supplying case which has a magazine shape into which the needle module is inserted like a bullet of a gun;
a withdrawing case which has a magazine shape into which the needle module is inserted like a bullet of a gun; and
a hair transplanter on which the supplying case and the withdrawing case are mounted and which transplants hair follicles into a scalp by sequentially operating needle modules in the supplying case one by one and inserts needle modules from which hair follicles are removed into the withdrawing case,
wherein the hair transplanter comprises:
a hair transplanter case in which a withdrawing case mounting groove and a body mounting groove are collinearly formed and a supplying case mounting groove is rectilinearly or obliquely formed between the withdrawing case mounting groove and the body mounting groove;
a body which is mounted on the body mounting groove of the hair transplanter case and comprises a roller guide groove formed at a rear thereof;
a moving device formed of any one or a combination of a roller, a ball, an opening, and a bearing mounted on the roller guide groove of the body;
a main shaft which has a hollow shape and an outer surface to which a connecting rod, which has one end coupled to the moving device, is fixedly coupled; and
a pressurizing bar which is inserted into the main shaft and pressurizes and transplants the hair follicle into the scalp.

9. The apparatus of claim 8, wherein the roller guide groove formed at the body comprises a linear portion formed therein and an inclined portion formed at a rear end part of the linear portion for a smooth movement and a peripheral disposition of the main shaft according to an operation of the moving device.

10. An automatic hair transplant apparatus comprising:
a supplying case having a magazine shape and supplying a needle module in a first direction, a hair follicle being inserted in the needle module;
a hair transplanter receiving the needle module from the supplying case, moving the received needle module in a second direction to transplant the hair follicle into a scalp, and transferring the needle module from which the hair follicle is removed in a third direction; and
a withdrawing case having a magazine shape and receiving the transferred needle module from the hair transplanter; wherein the first direction is perpendicular to the second direction, and the third direction is perpendicular to a plane defined by the first direction and the second direction.

11. The apparatus of claim 10, wherein each of the supplying case and the withdrawing case comprises:
a cover which comprises an accommodation space formed therein and an opening formed at a top or bottom thereof;
a pressurizing spring inserted into the accommodation space and located opposite the opening of the cover; and
a support plate mounted in the accommodation space and located between the pressurizing spring and the opening.

* * * * *